United States Patent [19]

Kenyhercz

[11] Patent Number: 4,486,423

[45] Date of Patent: Dec. 4, 1984

[54] STABLE FENTANYL COMPOSITION

[75] Inventor: Thomas M. Kenyhercz, Hillsborough, N.J.

[73] Assignee: Janssen Pharmaceutica Inc., Piscataway, N.J.

[21] Appl. No.: 487,349

[22] Filed: Apr. 21, 1983

[51] Int. Cl.$^3$ ............................................ A61K 31/445
[52] U.S. Cl. .................................................... 424/267
[58] Field of Search ......................................... 424/267

Primary Examiner—Stanley J. Friedman
Attorney, Agent, or Firm—Geoffrey G. Dellenbaugh

[57] ABSTRACT

Low pH formulations of fentanyl and related compounds have greatly improved stability and may be used in pre-filled syringes in contact with a rubber stopper.

8 Claims, No Drawings

STABLE FENTANYL COMPOSITION

BACKGROUND OF THE INVENTION

1. Field of the Invention

This invention relates to stable compositions of acidic fentanyl-like drugs and particularly to compositions of fentanyl citrate which are suitable for use in pre-filled syringes.

2. Description of the Prior Art

Fentanyl is the generic name for the compound N-(1-phenethyl-4 piperidyl) propionanilide, a useful injectable analgesic and anesthetic disclosed in U.S. Pat. No. 3,164,600, which is incorporated herein by reference. It has been sold for many years in the United States and elsewhere as the citrate salt under the tradename SUBLIMAZE. Fentanyl has also been sold for many years in the United States and elsewhere in combination with a material whose generic name is droperidol, this combination being sold under the tradename INNOVAR.

Other acidic fentanyl-like compounds include alfentanil, lofentanil, carfentanil, and sufentanil. Other acidic injectable compounds are etomidate and lorcainide. These compounds and others are disclosed in U.S. Pat. Nos. 4,167,574; 3,998,834; 3,354,173; and 4,126,089.

The fentanyl citrate composition sold in the United States comprises fentanyl citrate, USP water for injection, and sufficient sodium hydroxide to raise the pH to 6.5. This prior art composition is referred to throughout this disclosure as the "high pH fentanyl composition". Although this material is reasonably stable in glass ampoules and has been sold in glass ampoules for many years, it has been found unstable when in contact with a rubber closure in (for example) a pre-filled syringe. This instability is sufficiently serious to markedly decrease the potency of this fentanyl composition in a matter of days when contained in conventional syringes.

A different fentanyl citrate composition has been sold in Europe consisting only of fentanyl annd USP water for injection without any deliberate pH adjustment. Because of the specifications for USP water for injection, this composition has a pH in the range of from 5.0 to 7.0. This formulation has also suffered from the same instability with respect to rubber closures as the United States formulation.

INNOVAR is sold as a similar aqueous composition, except that the pH is adjusted to between 3.2 and 3.8. Droperidol (sold by itself under the tradename INAPSINE) is also sold as an aqueous composition having a pH between 3.0 and 3.8.

In the early 1970's, research was conducted on behalf of the company then selling fentanyl to determine the compatibility of a series of rubber closures with the high pH fentanyl citrate composition. This research determined that all 8 closure materials absorbed fentanyl and concluded that "[t]he possibility of packaging Fentanyl Citrate in a container with a rubber closure is rather dim unless the closure is either laquered or film coated or of a material with an extremely non-pourous unreactive surface. The potential for significant loss of drug exists because of the relatively low concentrations of Fentanyl Citrate in solution."

It has now surprisingly and unexpectedly been found that a reduction in the pH of the fentanyl citrate composition from the current 6.5 region to a range of from about 2.0 to about 3.8 yields not only excellent stability in contact with rubber closures but also greatly improved stability in glass ampoules. In fact, the subject low pH fentanyl formulation is more stable in a variety of commercial syringes then is the prior art high pH formulation in glass ampoules. When the low pH composition is stored in glass ampoules, it is virtually unchanged after 18 months at 50° C.

One sort of syringe which is particularly suited to be pre-filled with the subject low pH fentanyl composition is that disclosed and claimed in U.S. Pat. No. 4,367,738, which is incorporated herein by reference.

SUMMARY OF THE INVENTION

The present invention relates to a composition of an acidic injectable compound having improved stability which consists essentially of said compound and water and which has a pH between 2.0 and 3.8. This pH range is achieved by addition of a pharmaceutically acceptable acid to the composition, such as hydrochloric, hydrobromic, lactic, or citric acid. The preferred composition consists essentially of fentanyl citrate and water and sufficient citric acid to lower the pH to between 2.0 and 3.8.

This composition possess significantly better stability in glass ampoules than the prior art high pH formula and, more importantly, is stable for a commercially useful period of time in contact with a rubber closure. The new composition thus permits the convenient sale of fentanyl citrate in a pre-filled syringe.

DETAILED DESCRIPTION OF THE INVENTION

The low pH fentanyl citrate composition of the invention consists essentially of fentanyl citrate, water, and a sufficient amount of a pharmaceutically acceptable acid to reduce the pH to from about 2.0 to about 3.8. The preferred pH range is from about 3.0 to about 3.25, while 3.2±0.2 is the optimum range.

The concentration of fentanyl citrate in the subject low pH composition is not critical. A concentration of from about 0.005 mg/ml to about 5.0 mg/ml is acceptable, with a concentration of from 0.005 to 0.5 mg/ml being preferred, and a concentration of 0.05±0.02 mg/ml being most preferred.

To prepare the preferred embodiment of the subject low pH fentanyl composition, a 0.05 mg/ml solution of fentanyl citrate is prepared in USP water for injection, and the resulting solution titrated to pH 3.2±0.2 with 1M citric acid in USP water for injection. The composition is then filtered and filled into the desired containers.

The improved stability of the subject low pH fentanyl composition compared to the prior art high pH composition is demonstrated by the following table, in which a fentanyl citrate concentration of 0.05 mg/ml is used throughout. The assay is conducted as set out in the entry for fentanyl citrate injection in United States Pharmacopoeia (USP) Volume XX.

TABLE I

| High pH fentanyl composition-glass ampoules | | | |
| --- | --- | --- | --- |
| | Assay (% of label claim) at storage temperature | | |
| Age, months | 21° C. | 40° C. | 50° C. |
| 3 | 97.8 | | |
| 6 | 100.2 | 97.5 | 94.7 |
| 9 | 93.5 | 93.6 | 90.2 |
| 13 | 95.1 | 94.9 | 89.1 |
| 18 | 94.2 | 91.4 | 78.4 |

TABLE II

| Low pH fentanyl composition-glass ampoules | | | |
|---|---|---|---|
| | Assay (% of label claim) at storage temperatures | | |
| Age, months | 21° C. | 40° C. | 50° C. |
| 3 | 100.3 | 100.4 | 100.4 |
| 5 | 101.8 | 100.6 | 100.4 |
| 8 | 97.5 | 96.7 | 96.7 |
| 12 | 100.4 | 100.4 | 97.7 |
| 17 | 99.7 | 97.9 | 98.5 |

TABLE III

| Low pH fentanyl composition - syringe A | | | |
|---|---|---|---|
| | Assay (% of label claim) at storage temperature | | |
| Age, months | 21° C. | 40° C. | 50° C. |
| 3 | 99.3 | 99.9 | 99.3 |
| 5 | 100.1 | 100.1 | 100.6 |
| 8 | 98.5 | 98.7 | 98.5 |
| 12 | 99.2 | 98.2 | 98.0 |
| 17 | 99.2 | 100.2 | 99.4 |

TABLE IV

| Low pH fentanyl composition - syringe B | | | |
|---|---|---|---|
| | Assay (% of label claim) at storage temperature | | |
| Age, months | 21° C. | 40° C. | 50° C. |
| 4 | 98.7 | | |
| 5 | 100.1 | 98.0 | 96.9 |
| 7 | 99.7 | 95.7 | 89.4 |
| 12 | 98.6 | 93.9 | 87.2 |
| 16 | 98.8 | 94.5 | 81.2 |

TABLE V

| Low pH fentanyl composition - syringe C | | | |
|---|---|---|---|
| | Assay (% of label claim) at storage temperature | | |
| Age, months | 21° C. | 40° C. | 50° C. |
| 3 | 101.6 | 102.5 | 101.9 |
| 5 | 101.2 | 100.8 | 101.4 |
| 8 | 99.0 | 97.1 | 99.0 |
| 12 | 97.1 | 99.9 | 100.8 |
| 17 | 101.0 | 99.2 | 97.9 |

The effect of various rubber closure materials on the prior art high pH fentanyl composition was previously determined using a different procedure, with unacceptable results. Because of the poor results, no parallel study in syringes was conducted for this prior art composition.

In this previous study, approximately 5 grams of rubber closures were placed in 100 ml of fentanyl citrate solution and maintained at either 25° C. or 100° C. with shaking and the percent fentanyl remaining was determined at periodic intervals. After 24 hours at 100° C., no more than 50% of the original fentanyl remained in solution for any of the 8 closure materials studied. In many instances, the percentage of fentanyl remaining was significantly less than 50%. After storage for 50 days at 25° C., approximately 90% of the original fentanyl remained in solutions incubated with 3 of the closure materials, while the compositions containing the remaining 5 closure materials retained less than 80% of the original amount of fentanyl. Since the U.S. patent specification for fentanyl citrate injection is 90.0%–100.0% of the labelled claim, it is clear that the prior art fentanyl composition could not receive an expiration date of even 90 days in a prefilled syringe and hence is not practically useful for such a syringe.

The significantly improved stability of the subject low pH fentanyl composition is apparent from the information presented above. Since the variability in the assay is ±3%, the results in Table II demonstate essentially no decrease in fentanyl concentration. This compares with a significant decrease in fentanyl concentration in Table I after 18 months even at 21° C., with correspondingly greater decreases at higher temperatures. The data in Tables III through V demonstrate the vastly improved stability of the low pH fentanyl composition in commercially available syringes. Virtually no decrease in fentanyl concentration was observed for syringe A or syringe C, while a moderate but acceptable decrease in fentanyl concentration was noted for syringe B. It should be observed that the stability of the subject low pH fentanyl composition in syringe B is greater than that of the commercial high pH fentanyl composition in glass ampoules.

Finally, although the testing of a high pH fentanyl composition in contact with a rubber closure was not conducted under the identical conditions as was the low pH fentanyl composition, the instability of the prior art composition under such conditions is readily apparent from the results presented above.

What is claimed is:

1. A fentanyl composition consisting essentially of fentanyl citrate, water, and a sufficient amount of a pharmaceutically acceptable acid to reduce the pH to 3.2±0.2.

2. The composition of claim 1 wherein the fentanyl cirtrate concentration is from about 0.005 mg/ml to about 0.5 mg/ml.

3. The composition of claim 1 wherein the fentanyl citrate concentration is about 0.05±0.02 mg/ml.

4. The composition of claim 1 wherein the pharmaceutically acceptable acid is hydrochloric acid, hydrobromic acid, lactic acid, or citric acid.

5. A fentanyl composition consisting essentially of fentanyl citrate, water, and a sufficient amount of citric acid to reduce the pH of the composition to 3.2±0.2.

6. The composition of claim 5 wherein the fentanyl citrate concentration is from about 0.005 mg/ml to about 5.0 mg/ml.

7. A pre-filled syringe containing the composition of claim 5.

8. The composition of claim 5 wherein the pH is from about 3.0 to about 3.25.

* * * * *